US00PP27124P2

(12) United States Plant Patent
van den Hoogen

(10) Patent No.: US PP27,124 P2
(45) Date of Patent: Aug. 30, 2016

(54) ***HYPERICUM* PLANT NAMED 'ALLCALYP'**

(50) Latin Name: *Hypericum hybrida*
Varietal Denomination: Allcalyp

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/544,616

(22) Filed: Jan. 28, 2015

(51) Int. Cl.
*A01H 5/02* (2006.01)

(52) U.S. Cl.
USPC ..... Plt./442

(58) Field of Classification Search
USPC ..... Plt./442, 226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'Allcalyp', characterized by its upright and outwardly spreading plant habit; vigorous growth habit; dark green-colored leaves; freely flowering habit and high fruit density; and glossy bright red-colored fruits.

1 Drawing Sheet

Botanical designation: *Hypericum hybrida.*
Cultivar denomination: 'ALLCALYP'.

BACKGROUND OF THE INVENTION

The present invention relates to a new and distinct cultivar of *Hypericum* plant, botanically known as *Hypericum hybrida*, typically grown as a cut-flower and hereinafter referred to by the name 'Allcalyp'.

The new *Hypericum* plant is a product of a planned breeding program conducted by the Inventor in Cuijk, The Netherlands. The objective of the breeding program is to create new *Hypericum* plants with strong stems and numerous attractive fruits.

The new *Hypericum* plant originated from an open-pollination in September, 2009 in Cuijk, The Netherlands of a proprietary selection of *Hypericum hybrida* identified as code number 7-17-11, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled greenhouse environment in Cuijk, The Netherlands in September, 2010.

Asexual reproduction of the new *Hypericum* plant by vegetative cuttings in a controlled greenhouse environment in Cuijk, The Netherlands since April, 2011 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allcalyp'.

These characteristics in combination distinguish 'Allcalyp' as a new and distinct *Hypericum* plant:

1. Upright and outwardly spreading plant habit.
2. Vigorous growth habit.
3. Dark green-colored leaves.
4. Freely flowering habit and high fruit density.
5. Glossy bright red-colored fruits.

Plants of the new *Hypericum* differ primarily from plants of the female parent selection in the following characteristics:

1. Plants of the new *Hypericum* produce larger fruits than plants of the female parent selection.
2. Plants of the new *Hypericum* and the female parent selection differ in fruit color as plants of the female parent selection have brownish red-colored fruits.

Plants of the new *Hypericum* can be compared to plants of the *Hypericum hybrida* 'Allgrando', not patented. In side-by-side comparisons, conducted in Cuijk, The Netherlands, plants of the new *Hypericum* differed primarily from plants of 'Allgrando' in the following characteristics:

1. Plants of the new *Hypericum* had smaller sepals than plants of 'Allgrando'.
2. Plants of the new *Hypericum* and 'Allgrando' differed in fruit color as plants of 'Allgrando' had purplish brown-colored fruits.

BRIEF DESCRIPTION OF THE PHOTOGRAPH

The accompanying colored photograph illustrates the overall appearance of the new *Hypericum* plant showing the colors as true as it is reasonably possible to obtain in colored reproductions of this type. Colors in the photograph may differ slightly from the color values cited in the detailed botanical-description which accurately describe the actual colors of the new *Hypericum* plant.

The photograph comprises a side perspective view of a flowering plant of 'Allcalyp' grown in a 10-cm container.

DETAILED BOTANICAL DESCRIPTION

Plants used for the aforementioned photographs and following description were grown in September in an outdoor nursery in Timau, Kenya and under cultural practices typical of commercial cut-flower *Hypericum* production. During the production of the plants, day temperatures ranged from 15° C. to 25° C. and night temperatures ranged from 5° C. to 15° C. Plants were one year old when the photograph and description were taken. In the following description, color references are made to The Royal Horticultural Society Colour Chart, 2007 Edition, except where general terms of ordinary dictionary significance are used.

Botanical classification: *Hypericum hybrida* 'Allcalyp'.

Parentage:

*Female, or seed, parent*.—Proprietary selection of *Hypericum hybrida* identified as code number 7-17-11, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures about 12° C. to 30° C.

*Time to initiate roots, winter*.—About 14 to 20 days at temperatures about 12° C. to 22° C.

*Time to produce a rooted young plant, summer*.—About 24 to 32 days at temperatures ranging from 12° C. to 30° C.

*Time to produce a rooted young plant, winter*.—About 28 to 36 days at temperatures ranging from 12° C. to 22° C.

*Root description*.—Fine, fleshy; white in color.

*Rooting habit*.—Freely branching; dense.

Plant description:

*Plant and growth habit*.—Perennial shrub; upright and outwardly spreading plant habit, narrow inverted triangle; vigorous growth habit.

*Branching habit*.—Moderately freely basal branching habit; pinching enhances lateral branch development.

*Plant height*.—About 85.5 cm.

*Plant width* (*spread*).—About 21.4 cm.

*Lateral branch description*.—Length: About 85.7 cm. Diameter: About 4 mm. Internode length: About 7.3 cm. Strength: Moderately strong to strong. Texture: Smooth, glabrous. Luster: Moderately glossy. Color, developing: Close to 183B to 183D; youngest stems tinged with close to 144A. Color, fully developed: Close to N199C to N199D.

Leaf description:

*Arrangement*.—Opposite, simple; sessile.

*Length*.—About 6.8 cm.

*Width*.—About 4.8 cm.

*Shape*.—Ovate.

*Apex*.—Retuse.

*Base*.—Truncate.

*Margin*.—Entire.

*Texture, upper and lower surfaces*.—Smooth to slightly rugose; glabrous.

*Luster, upper and lower surfaces*.—Slightly glossy.

*Venation pattern*.—Pinnate.

*Color*.—Developing leaves, upper surface: Close between 144A and 137C. Developing leaves, lower surface: Close to 137C. Fully expanded leaves, upper surface: Darker than between 147A and N189A; venation, close to 144A. Fully expanded leaves, lower surface: Close to between 138B and 147B; venation, close to 144B.

Flower description:

*Flower type, arrangement and flowering habit*.—Single rotate flowers arranged in terminal and axillary compound cymes; freely flowering habit with about twelve flowers per cyme; flowers face mostly upright.

*Fragrance*.—None detected.

*Natural flowering season*.—Plants flower continuously from mid- June to mid-August in Kenya; plants begin flowering about ten months after planting.

*Flower longevity*.—Flowers last about two or three days on the plant; flowers not persistent.

*Fruit longevity*.—About one month on the plant.

*Flower buds*.—Length: About 7 mm. Diameter: About 7 mm. Shape: Globular. Color: Close to 151C; towards the apex, close to 21B.

*Inflorescence height*.—About 11.7 cm.

*Inflorescence diameter*.—About 7.2 cm.

*Flower diameter*.—About 2.9 cm.

*Flower depth* (*height*).—About 2.2 cm.

*Petals*.—Quantity and arrangement: Five in a single whorl. Length: About 1.35 cm. Width: About 1 cm. Shape: Ovate; concave; very slightly reflexed. Apex: Bluntly acute. Base: Attenuate. Margin: Entire. Texture, upper and lower surfaces: Smooth, glabrous. Luster, upper surface: Matte. Luster, lower surface: Slightly glossy. Color: When opening and fully opened, upper surface: Close to 12A; color becoming closer to 14B with development. When opening and fully opened, lower surface: Close to 13B.

*Sepals*.—Quantity and arrangement: Five in a single whorl. Length: About 9 mm. Width: About 7 mm. Shape: Broadly ovate; moderately to strongly reflexed. Apex: Broadly acute to obtuse. Base: Broadly cuneate. Margin: Entire. Texture, upper and lower surfaces: Smooth, glabrous. Luster, upper and lower surfaces: Dull, matte. Color: When opening, upper surface: Close to 143A. When opening, lower surface: Close to 143C. Fully opened, upper surface: Close to between 141A and 143A. Fully opened, lower surface: Close to 143C.

*Peduncles*.—Length: About 2.7 cm. Diameter: About 2 mm. Texture: Smooth, glabrous. Strength: Moderately strong. Aspect: Erect to about 50° from vertical. Color: Close to 176A.

*Pedicels*.—Length: About 1.6 cm. Diameter: About 1.5 mm. Texture: Smooth, glabrous. Strength: Moderately strong. Aspect: Erect to about 50° from vertical. Color: Close to 144B to 144C strongly tinged with close to 176A.

*Reproductive organs*.—Stamens: Quantity per flower: About 80. Filament length: About 1.5 mm. Filament color: Close to 12A. Anther length: About 0.5 mm. Anther shape: Broadly oval. Anther color: Close to 22A. Pollen amount: Scarce. Pollen color: Close to 11A. Pistils: Quantity per flower: Single pistil with three stigmas. Pistil length: About 4 mm. Stigma shape: Club-shaped. Stigma color: Close to 35A. Style length: About 3.5 mm. Style color: Close to 150C. Ovary color: Close to 150D.

*Fruits*.—Length: About 1.6 cm Diameter: About 1.6 cm. Shape: Spherical. Texture: Smooth, glabrous. Luster: Glossy. Color: Close to 46A; towards the base, close to 49B to 49D.

*Seeds*.—Length: About 0.9 mm. Diameter: About 0.5 mm. Color: Close to 200A.

Disease & pest resistance: Plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allcalyp' as illustrated and described.

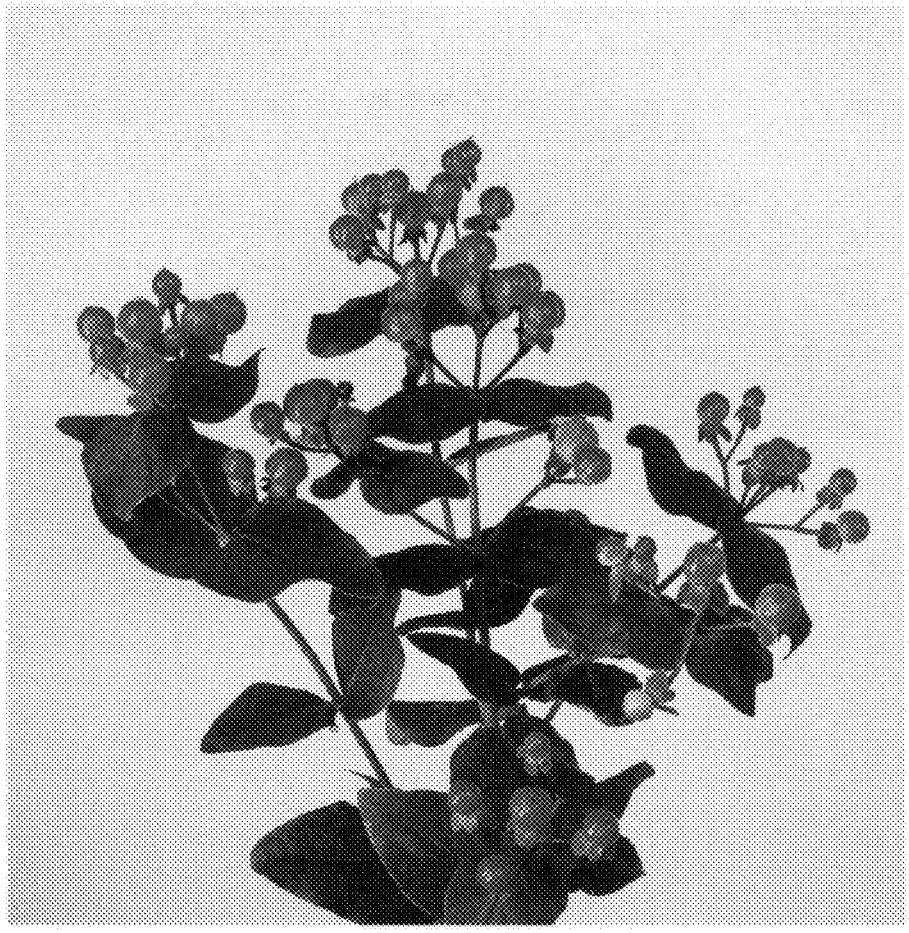

* * * * *